(12) United States Patent
Finger et al.

(10) Patent No.: US 11,045,665 B2
(45) Date of Patent: *Jun. 29, 2021

(54) LIGHT-GUIDED OPHTHALMIC RADIATION DEVICE

(71) Applicant: IP LIBERTY VISION CORPORATION

(72) Inventors: Paul T. Finger, New York, NY (US); Toby Welles, New York, NY (US)

(73) Assignee: IP Liberty Vision Corporation, New York, NY (US)

(*) Notice: Subject to any disclaimer, the term of this patent is extended or adjusted under 35 U.S.C. 154(b) by 253 days.

This patent is subject to a terminal disclaimer.

(21) Appl. No.: 16/240,733

(22) Filed: Jan. 5, 2019

(65) Prior Publication Data
US 2019/0240506 A1 Aug. 8, 2019

Related U.S. Application Data

(63) Continuation of application No. 14/440,881, filed on May 6, 2015, now Pat. No. 10,173,075.

(51) Int. Cl.
*A61N 5/10* (2006.01)
*A61B 1/07* (2006.01)
(Continued)

(52) U.S. Cl.
CPC .............. *A61N 5/1017* (2013.01); *A61B 1/07* (2013.01); *A61N 5/1007* (2013.01); *A61B 1/05* (2013.01); *A61B 2090/306* (2016.02); *A61N 2005/1008* (2013.01); *A61N 2005/1021* (2013.01); *A61N 2005/1094* (2013.01)

(58) Field of Classification Search
CPC .......... A61N 5/1017; A61N 2005/1094; A61B 1/07; A61B 2090/306
See application file for complete search history.

(56) References Cited

U.S. PATENT DOCUMENTS

| 4,545,337 A | 10/1985 | Lyons et al. |
| 5,637,073 A | 6/1997 | Freire |

(Continued)

FOREIGN PATENT DOCUMENTS

| CN | 2136646 Y | 6/1993 |
| WO | WO 2006/125106 A1 | 11/2006 |
| WO | WO 2009/089288 A1 | 7/2009 |

OTHER PUBLICATIONS

International Search Report for PCT Application No. PCT/US13/68944 dated Apr. 10, 2014.
(Continued)

*Primary Examiner* — Kaylee R Wilson
(74) *Attorney, Agent, or Firm* — Smith Tempel; Steven P. Wigmore

(57) ABSTRACT

An ophthalmic radiation device having a substantially light-transparent wand configured to emit light propagating through the wand light from a series of illumination ports at least partially circumscribing a radioactive source disposed in the holder, thereby providing a visual reference for identifying a position of the radioactive source. Embodiments are directed at effectively directing light from a light source through the body of the wand to illumination ports by using the wand body itself as the light guide. The illumination ports are used as reference points by a medical practitioner to facilitate placing the device into a correct treatment position.

20 Claims, 16 Drawing Sheets

(51) Int. Cl.
*A61B 90/30* (2016.01)
*A61B 1/05* (2006.01)

(56) References Cited

U.S. PATENT DOCUMENTS

| | | | |
|---|---|---|---|
| 6,270,491 | B1 | 8/2001 | Toth et al. |
| 6,413,245 | B1 | 7/2002 | Yaacobi et al. |
| 6,443,881 | B1 | 9/2002 | Finger ................. A61N 5/0601 |
| | | | 600/1 |
| 7,070,554 | B2 | 7/2006 | White et al. |
| 7,351,193 | B2 | 4/2008 | Forman et al. |
| 7,862,496 | B2 | 1/2011 | Hermann et al. |
| 2004/0138515 | A1 | 7/2004 | White ................. A61N 5/1017 |
| | | | 600/3 |
| 2004/0201980 | A1 | 10/2004 | Fischer ............... A61B 5/0088 |
| | | | 362/84 |
| 2006/0078087 | A1 | 4/2006 | Forman ............... A61N 5/1001 |
| | | | 378/65 |
| 2006/0256575 | A1 | 11/2006 | Vayser ................ A61B 1/0623 |
| | | | 362/573 |
| 2007/0106108 | A1 | 5/2007 | Hermann et al. |
| 2007/0260231 | A1 | 11/2007 | Rose .................... A61B 18/22 |
| | | | 606/13 |
| 2010/0004499 | A1 | 1/2010 | Brigatti et al. |
| 2010/0004581 | A1 | 1/2010 | Brigatti et al. |

OTHER PUBLICATIONS

Supplementary European Search Report for European Application No. 13853945.7 dated Feb. 10, 2017.

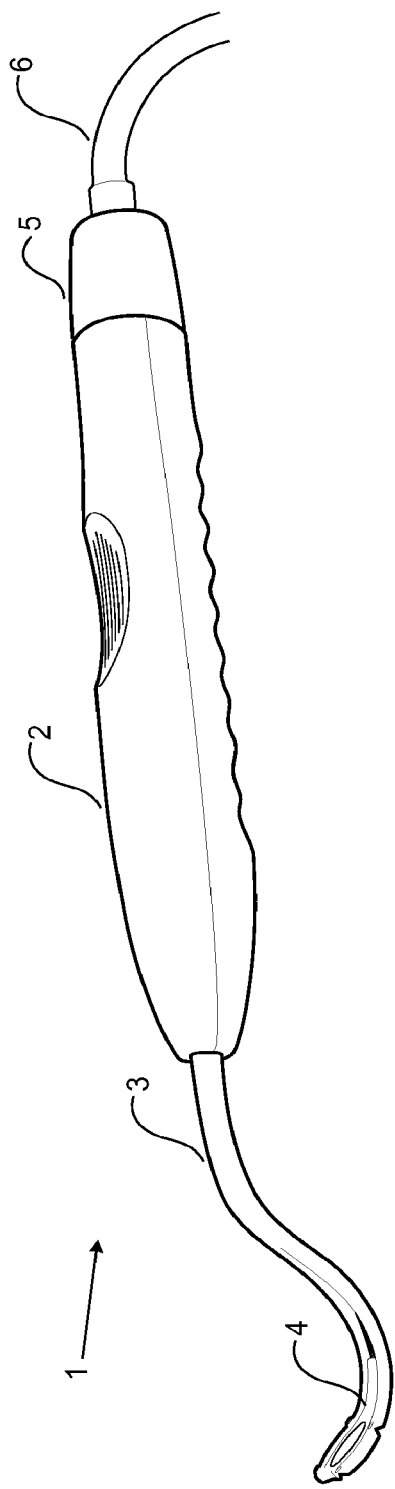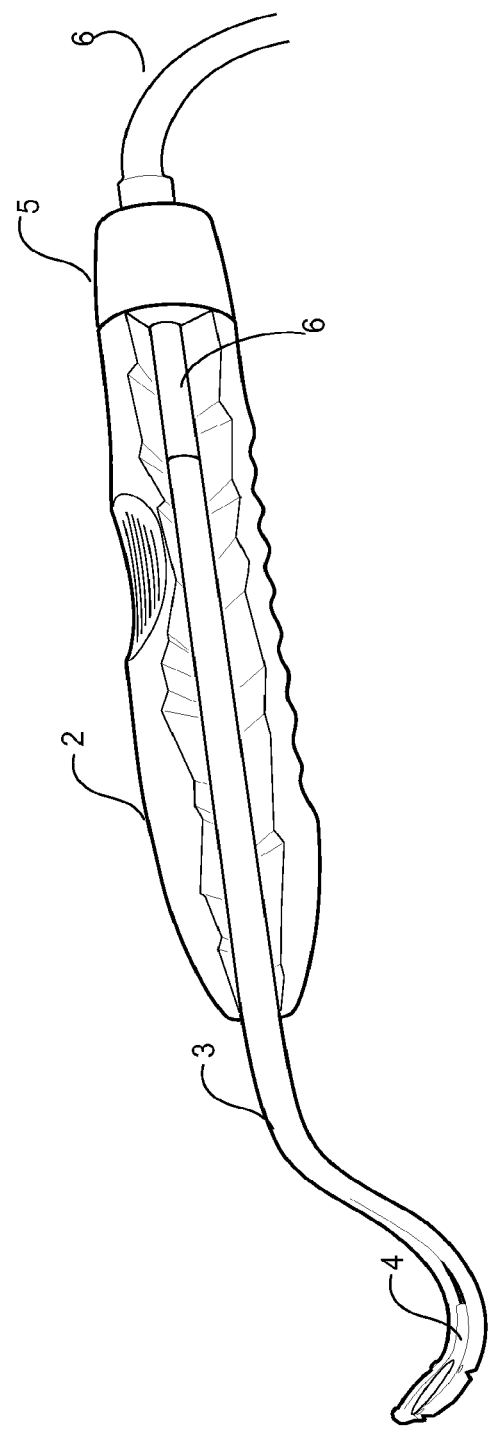
FIG. 1
FIG. 1A

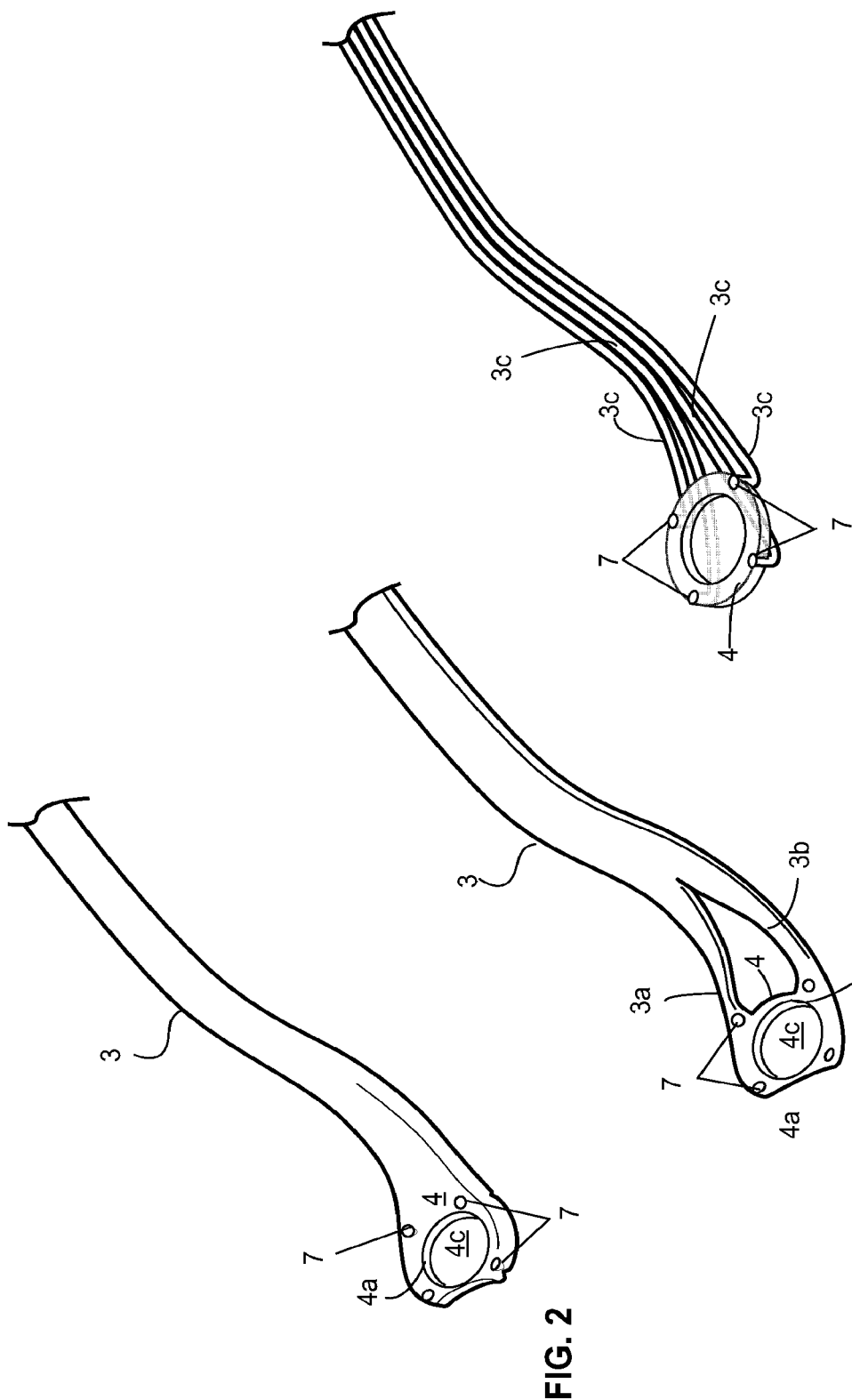

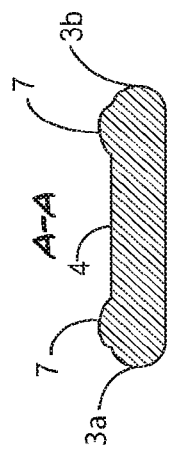
FIG. 3B A-A
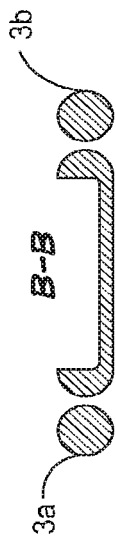
FIG. 3C B-B
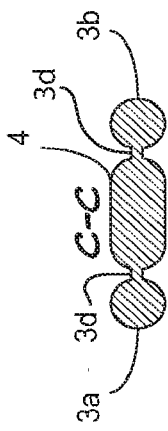
FIG. 3D C-C
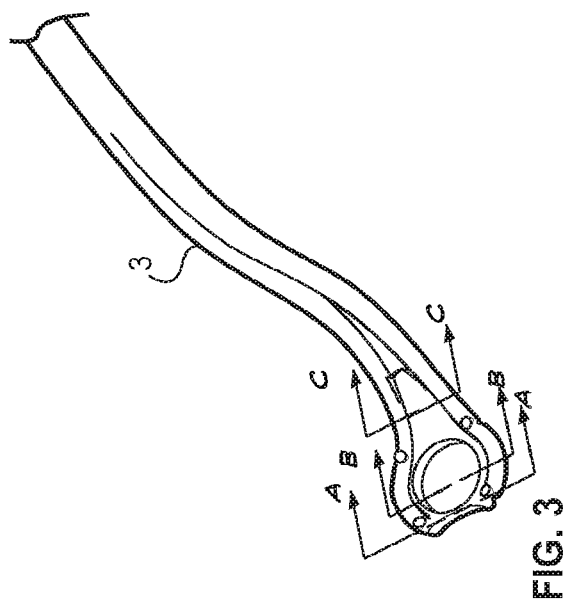
FIG. 3
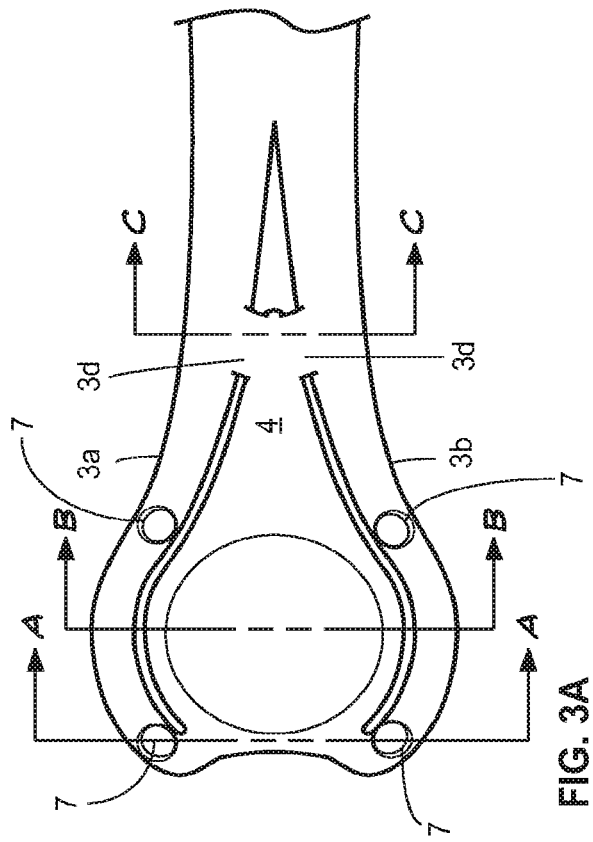
FIG. 3A

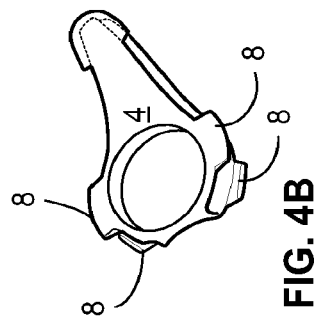
FIG. 4B
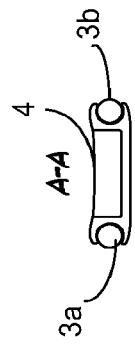
FIG. 4C
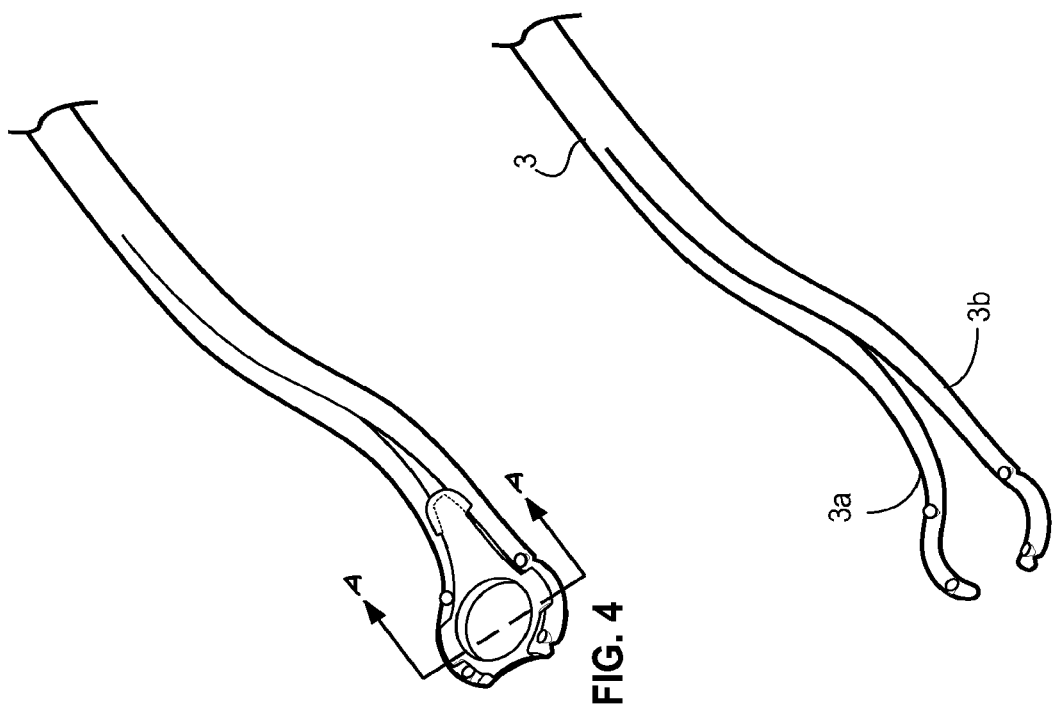
FIG. 4
FIG. 4A

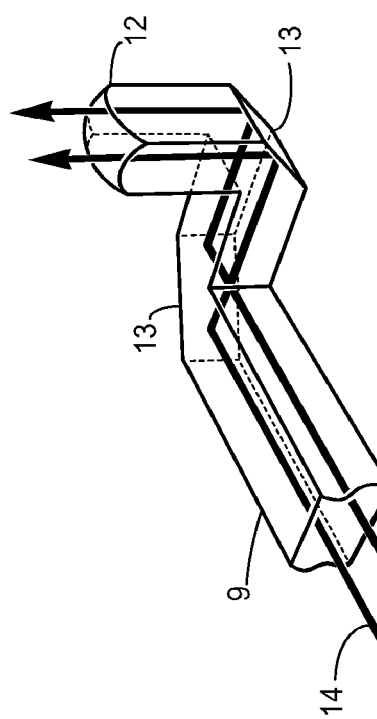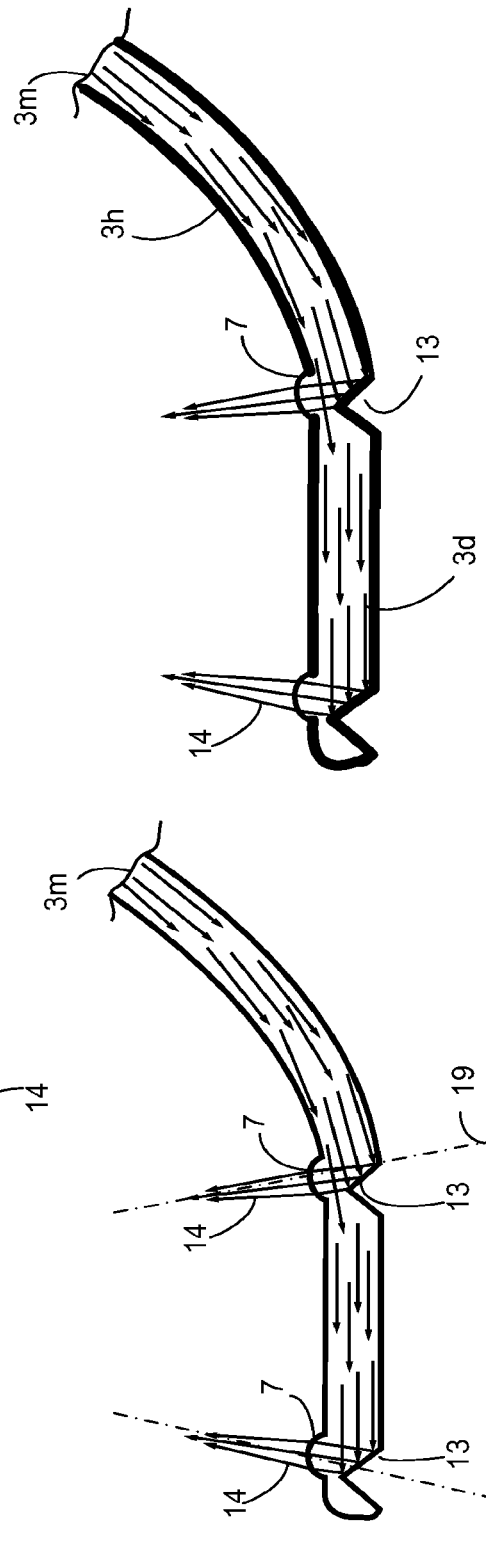

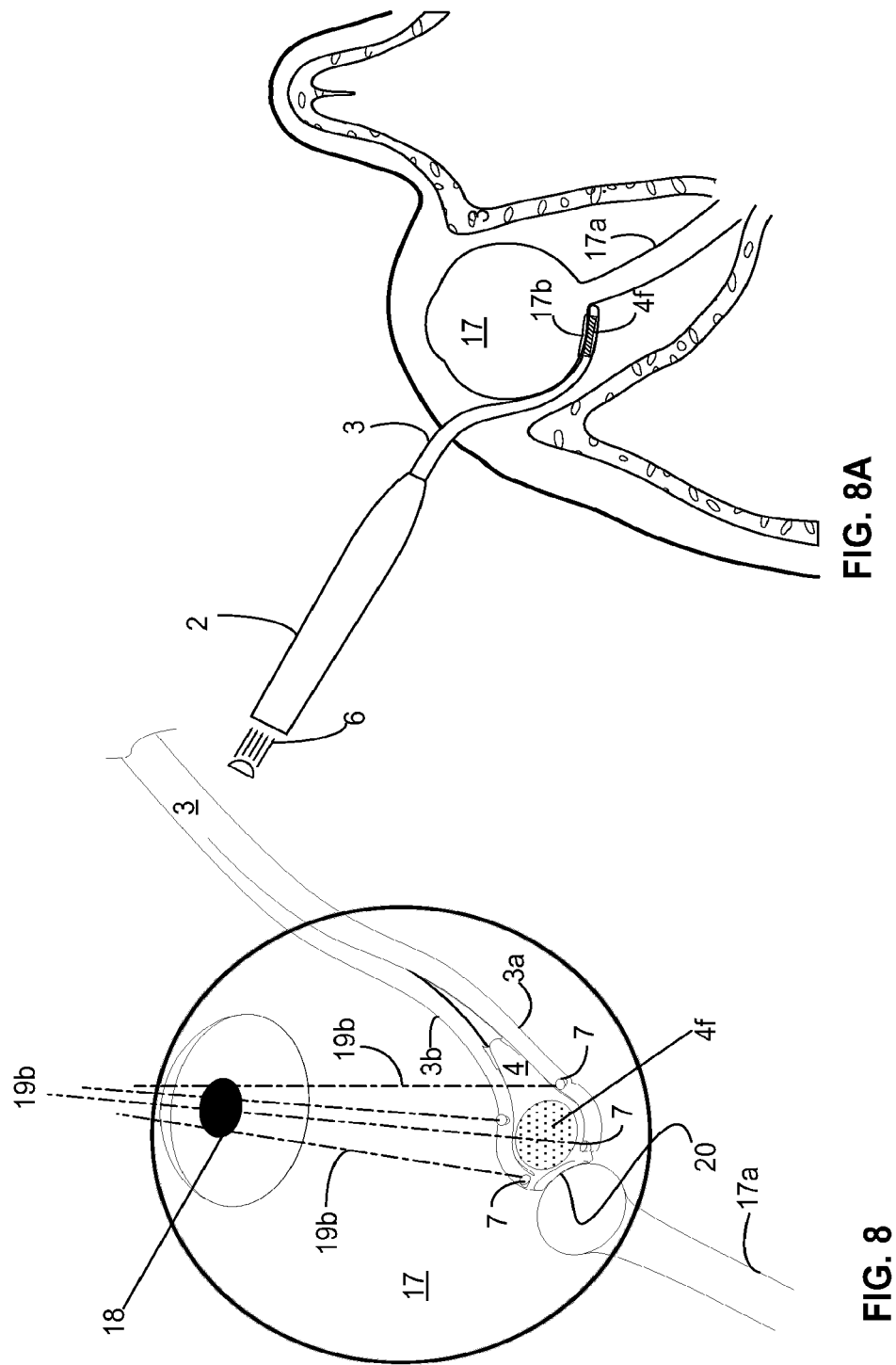

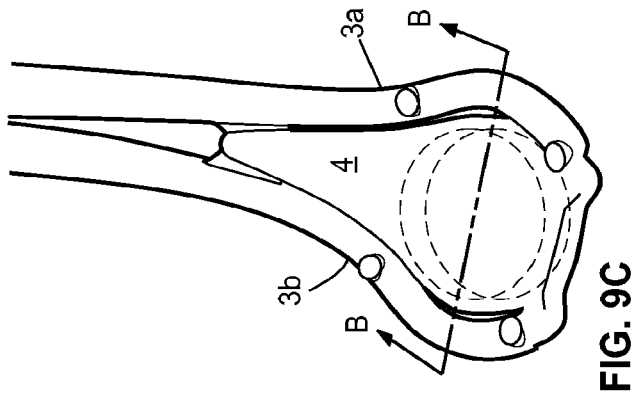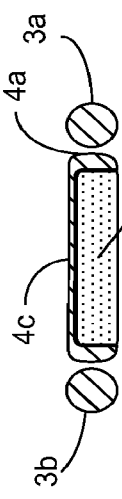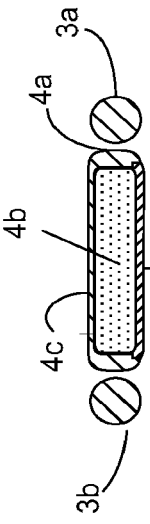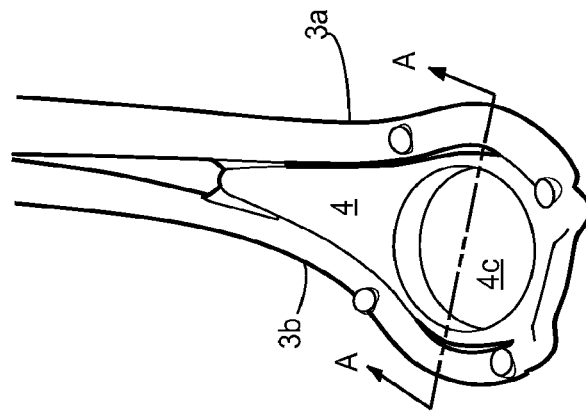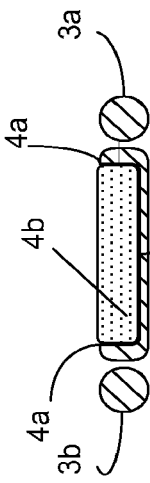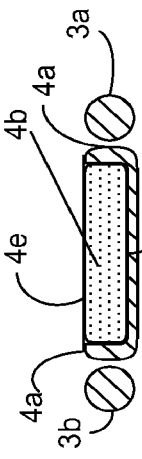

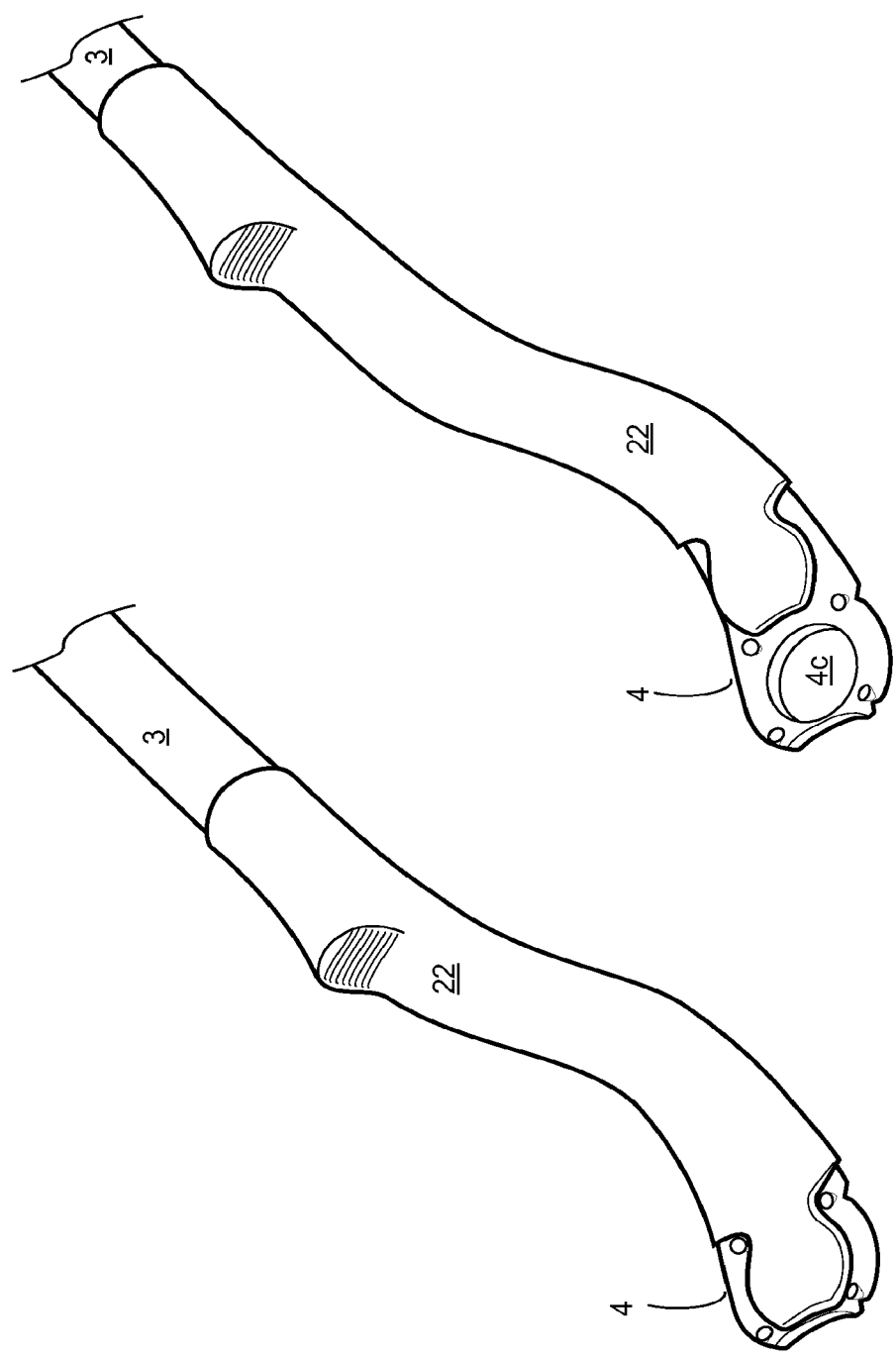

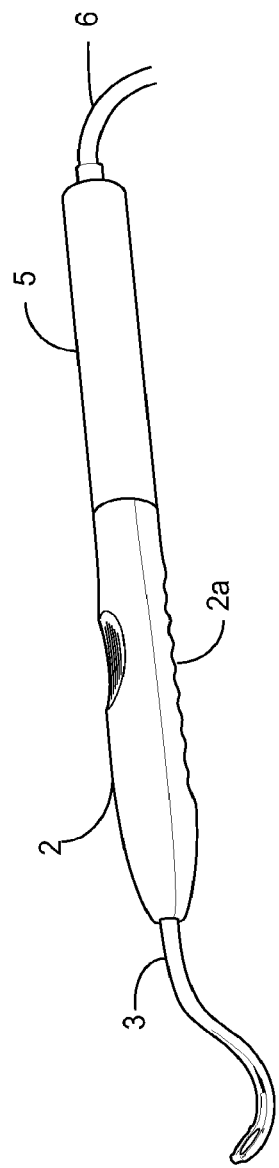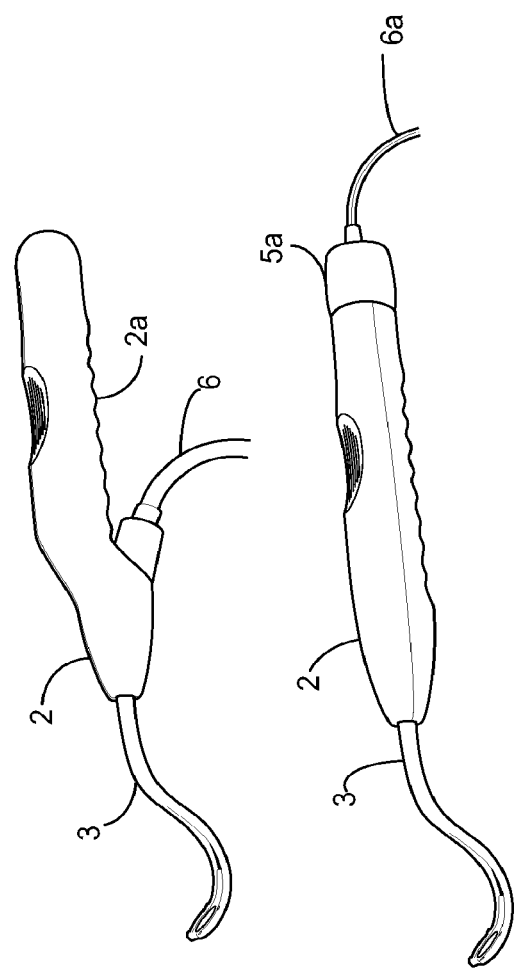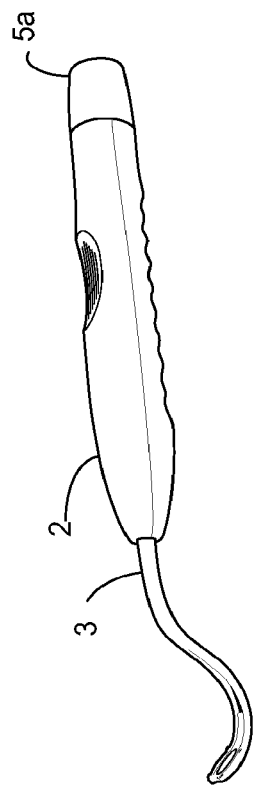
FIG. 13
FIG. 13A
FIG. 13B
FIG. 13C

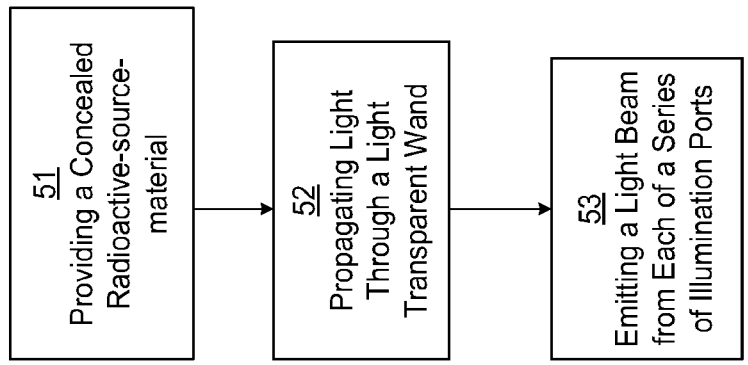
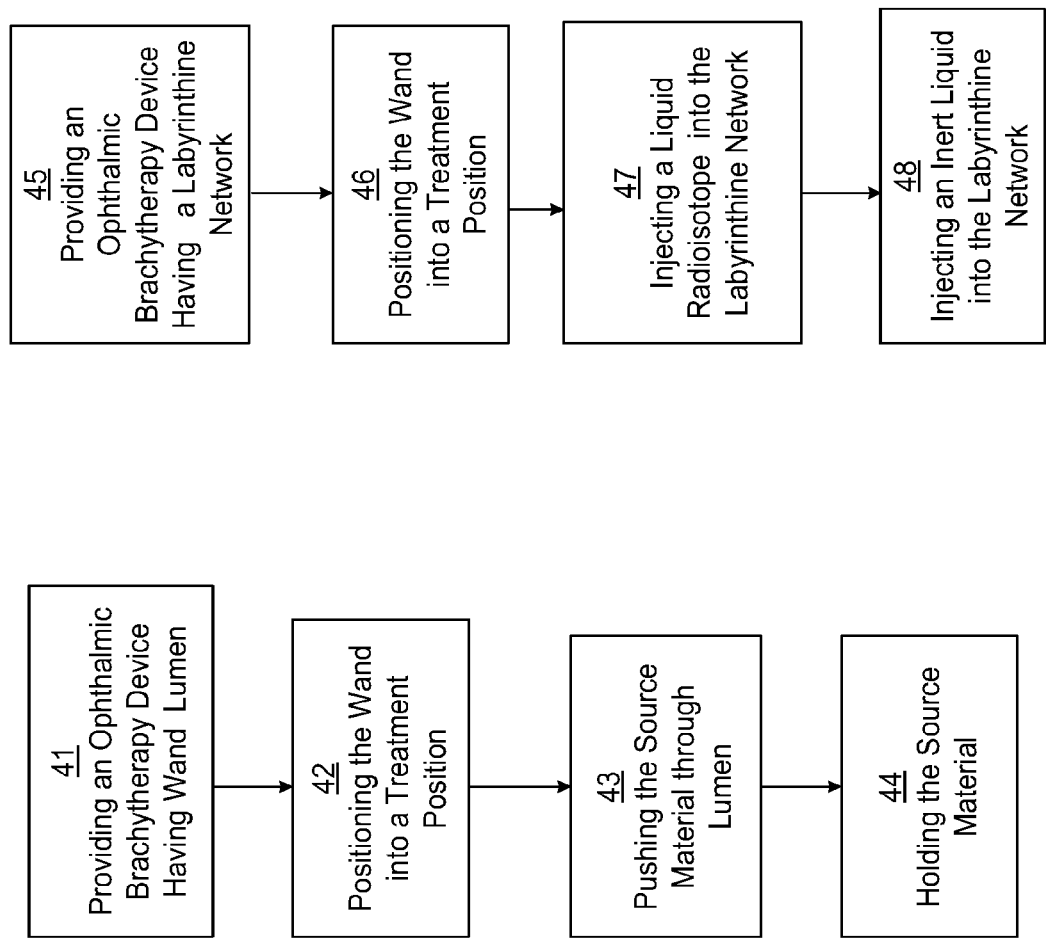
FIG. 15B
FIG. 15A
FIG. 15

LIGHT-GUIDED OPHTHALMIC RADIATION DEVICE

FIELD AND BACKGROUND OF THE INVENTION

The present invention relates generally to ophthalmic radiation device for directing a therapeutic dose of radiation to a portion of the eye to treat subretinal neovascularization associated with age-related macular degeneration (AMD) and other ophthalmic diseases responsive to irradiation.

Exudative macular degeneration is a pathologic process associated with subretinal neovascularization. The subretinal neovascularization allows fluid, blood, and lipids to leak beneath the surface of the retina. This leakage has detrimental effects on the health of the globe. For example, this leakage typically causes retinal detachment and destroys the macular retina resulting in severe damage including irreversible loss of central vision.

BRIEF DESCRIPTION OF THE DRAWINGS

The subject matter regarded as the invention is particularly pointed out and distinctly claimed in the concluding portion of the specification. The invention, in regards to its features, components and their configuration, operation, and advantages are best understood with reference to the following description and accompanying drawings in which:

FIG. 1 is a general, schematic perspective view of an ophthalmic radiation treatment device, according to an embodiment;

FIG. 1A is a cutaway view of the handle of FIG. 1;

FIG. 2 is schematic, perspective view of an embodiment of a radiation treatment device depicting a radioactive source holder integrally connected to a treatment wand in which both are configured to function as an integral light guide, according to an embodiment;

FIG. 2A is schematic, perspective view of variant embodiment of the device depicted in FIG. 2 in which the treatment wand forks into two wand branches, FIG. 1;

FIG. 2B is schematic, perspective view of another embodiment of the device depicted in FIG. 1 in which the holder is non-integrally attached to the wand implemented as multiple light pipes, according to an embodiment;

FIGS. 3-3A are schematic, perspective views of an embodiment of the radiation treatment device in which the holder is connected to distal portions of each of two wand branches, according to an embodiment;

FIGS. 3B, 3C, and 3D are schematic cross-sectional views along section lines A-A, B-B, and C-C depicted in FIGS. 3-3A, respectively;

FIG. 4 is schematic perspective view of a variant embodiment of the device depicted in FIGS. 3-3D in which the holder is releasably attachable to each of the wand branches, according to an embodiment;

FIG. 4A is schematic perspective view of the treatment wand depicted in FIG. 4 detached from the holder, according to an embodiment;

FIG. 4B is schematic perspective view of the holder depicted in FIG. 4 detached from the wand, according to an embodiment;

FIG. 4C is schematic cross-sectional view of the device depicted in FIG. 4 along section line A-A according to an embodiment;

FIG. 6 is schematic, perspective view of an integral prismatic surface molded into the wand branch, according to an embodiment;

FIG. 6A is schematic, perspective view of a wand branch having both integral prismatic light redirecting surfaces, and focusing lens according to an embodiment;

FIG. 6B is schematic, perspective view of a variant embodiment of the wand branch of FIG. 6A having an opaque film selectively disposed on the surface to minimize unwanted light emission through the wand, according to an embodiment;

FIG. 8 is a schematic, perspective view of the ophthalmic radiation device disposed in a treatment position behind an eyeball in which the illumination ports surrounding the holder are visible through the pupil, according to an embodiment;

FIG. 8A is a schematic, section view of the ophthalmic radiation device disposed in a treatment position behind an eyeball in which the radiation source is in proximity to the a macula, according to an embodiment;

FIG. 9 is a schematic, perspective view of a radioactive source-material holder having a holding cavity facing the eye, according to an embodiment;

FIG. 9A is a schematic, cross-sectional view of the holder depicted in FIG. 9 along section line A-A; according to an embodiment;

FIG. 9B is a schematic, cross-sectional view along section line A-A of a variant embodiment of the holder of FIG. 9 in which the holding cavity is enclosed with a cover; according to an embodiment;

FIG. 9C is a schematic, perspective view of radioactive source-material holder having a holding cavity facing the skull orbit, according to an embodiment;

FIG. 9D is a schematic, cross-sectional view of the holder depicted in FIG. 9C along section line B-B; according to an embodiment;

FIG. 9E is a schematic, cross-sectional view along section line B-B of a variant embodiment of the holder of FIG. 9C in which the holding cavity is enclosed with a cover; according to an embodiment;

FIGS. 10 and 10A are schematic, perspective views of an ophthalmic radiation device fitted with a radiation-shielding sleeve in shielded and non-shielded states, respectively, according to an embodiment;

FIG. 12A is a schematic, perspective view of ophthalmic radiation device depicted in FIG. 12 in which the liquid therapeutic-radio isotope is disposed in the labyrinthine holder, according to an embodiment;

FIG. 12B is a schematic side view of a double-sided piston pump configured to simultaneously inject liquid radioisotope and withdraw inert liquid from the labyrinthine holder depicted in FIGS. 12 and 12A, according to an embodiment; and FIG. 13 is a schematic, perspective view of the ophthalmic radiation device in which light is directed into the device from an external light source, according to an embodiment;

FIG. 13A is a schematic, perspective view of a ophthalmic radiation device in that the light is directed into the handle in close proximity to a handle grip at an angle non-parallels to the longitudinal axis of the handle, according to an embodiment;

FIG. 13B is a schematic, perspective view of the ophthalmic radiation device in which a light source is disposed in the device and powered from an external power source, according to an embodiment; and FIG. 13C is a schematic, perspective view of the ophthalmic radiation device in which both a light and power sources are self-contained inside the device, according to an embodiment.

FIG. 15 is a flow chart depicting a process for advancing a radioactive-source-material into an ophthalmic radiation device after the device has been placed into a treatment position; according to an embodiment;

FIG. 15A is a flow chart depicting a process for inserting a liquid radioactive isotope into the ophthalmic radiation device after placement into a treatment position; according to an embodiment; and FIG. 15B is a flow chart depicting a method for visually identifying a position of a concealed radioactive source material according to an embodiment;

Figure 5D:
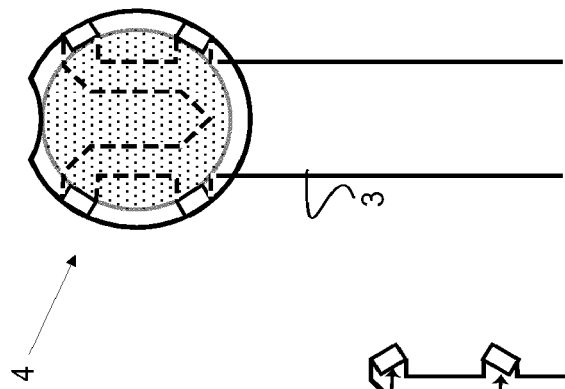
FIGS. 5C and 5D are schematic, front views of a variant embodiment of the device depicted in FIG. 5B having an alternative branching configuration, according to an embodiment.

It will be appreciated that for clarity elements shown in the figures may not be drawn to scale. For example, the dimensions of some of the elements may be exaggerated relative to other elements for clarity. Furthermore, where considered appropriate, reference numerals may be repeated among the figures to indicate corresponding or analogous elements.

DETAILED DESCRIPTION OF EMBODIMENTS THE PRESENT INVENTION

In the following detailed description, numerous details are set forth in order to provide a thorough understanding of the invention. However, it will be understood by those skilled in the art that the present invention may be practiced without these specific details and that well-known methods, procedures, and components have not been described in detail so as not to obscure the present invention.

Embodiments of the present invention are generally directed to an ophthalmic radiation device and treatment method facilitating placement of a therapeutic radioisotope onto or near the eyeball and within its socket as noted above. Specifically, embodiments are directed at effectively directing light from a light source through the body of the wand to illumination ports by using the wand body itself as the lightguide. The illumination ports are used as reference points by a medical practitioner to facilitate placing the device into a correct treatment position.

The following terms will be used out through the document:

"Radioactive-source-material", "source", "source material", or "radiation source" all refer to a radioactive material providing the therapeutic dose of radiation. Non-limiting examples of a therapeutic-radioisotope include, inter alias, Yttrium, and Strontium "Holder" refers to a structure for supporting or containing a therapeutic quantity of a radioactive source material. The holder may be configured to contain the source material in either solid or liquid form as will be further discussed.

"Wand", "treatment wand", "body of the wand", or "wand body" refer to an elongated ergonomic structure extending from a handle and supporting the holder at its distal end, according to an embodiment. The wand is contoured to provide the optimal access, visibility, and control, and fatigue-preventive ergonomics for the surgeon. The wand is light transmissive and has minimal surface features so as to minimize light dissipation through the body of wand.

"Medicinal agent" refers to therapeutic agents like, inter alia, a drug or a chemical, visible light, non-visible electromagnetic radiation, or particle radiation.

"Medical practitioner" refers to surgeons, doctor, nurse, or any other personnel applying or assisting in applying a radiation treatment.

"Distal" and "proximal" are relative terms of position measured in terms of positional relationship to the end of handle closest to the user holding the device. Accordingly, "distal" refers to the point or portion most distant from the end of the handle closest to the user holding the handle, whereas "proximal" refers to a point or portion nearest to the end of the handle closest to the user holding the handle "Distal portion" refers to a position near the distant extremity; but, does not necessarily include the most distant point.

"Light guide" refers to substantially transparent solid body through which light propagation is directed in accordance with the surface geometry of the body. "Light pipe" refers to a specific type of light guide implemented as a fiber. "Illumination source light pipe" refers to an optic fiber.

"Opaque" refers to a state that is either non-transparent, non-translucent, or impenetrable by light.

"Catch element" refers to a structure securing the radiation-source-material in a single to location in lumen of a wand. Accordingly, a wall bulge constricting the cross-sectional area of the lumen is also deemed to be a catch element.

"Circumscribe" refers to surrounding even if the source is non-circular.

In addition to the administration of therapeutic doses of radiation in the treatment of AMD, melanoma, and other eye ailments responsive to radiation, the device may also be used to administer a drug or therapeutic substances released from body of the device into, through or onto the sclera or other associated tissues or attach specialized medicinal agents to the sclera itself, according to an embodiment.

Turning now to the figures, FIG. 1 depicts an ophthalmologic radiation device, generally labeled 1, enabling a medical practitioner to apply a therapeutic dose of radiation to the target tissue. In anon-limiting embodiment device 1 includes a radioactive-source-material holder 4, a handle 2, a light pipe in communication with a light source coupling 5 for connecting the light pipe 6 to handle 5, and a treatment wand 3 for inserting the radioactive-source-material near the target tissue.

Wand 3 may be constructed of strong, substantially light transparent polymeric material such as polycarbonate or polysulfone, for example, or other material providing mechanical integrity and transparency enabling light to propagate through the wand 3. In certain embodiments the wand 3 is releasably attachable to handle 2 while in other embodiments wand is permanently attached to handle 2.

As shown in FIG. 1A, wand 3 extends into the body of handle 2 and abuts light pipe 6 held inside handle 2 by coupling 5 to enable light to propagate through wand 3 from light pipe 6 to the distal end of the wand 3 near holder 4, according to a certain embodiment. It should be appreciated that in certain embodiments non-abutment connection configurations between illuminations source 6 and wand 3 may be employed.

FIGS. 2-2B depict various wand embodiments through which light is directed from the illuminations source to a series of illumination ports 7 circumscribing a radiation source disposed in holder 4, according to certain embodiments. The emitted light beams advantageously provide a visual reference useful in identifying the position of a radioactive source material disposed in holder 4.

Specifically, FIG. 2 depicts a wand 3 integrally connected to holder 4 so as to enable light emission through illumination ports 7 and also holder floor, 4c, holder wall 4a, or both, according to an embodiment. It should be appreciated that in such embodiments both holder 4 and the wand 3 are constructed from similar or identical light transmissive material.

FIG. 2A depicts a variant embodiment of the wand depicted in FIG. 2 in which a wand 3 forks into two branches, 3a and 3b, integrally connected to holder 4 so as to enable light emission through illumination ports 7 and also holder floor 4c, holder wall 4a, as described previously. In a certain embodiment, holder 4 is configured to prevent light emission through any part of the holder and so that substantially all light emission occurs at illumination ports 7.

FIG. 2B depicts another variant embodiment of the wand and holder depicted in FIG. 2 in which wand 3 is implemented as four independent light pipes 3c enabling independent light propagation through each light pipe 3c to illumination ports 7 disposed in holder 4. It should be appreciated that any plurality of light pipes 3c is included within the scope of the present invention.

In a certain embodiment, illumination of each light pipe 3c is implemented with light of different wavelengths while in another embodiment light pipes 3c are illuminated non-simultaneously.

It should also be appreciated that various combinations of illumination wavelengths and timing are included in the scope of the present invention.

FIGS. 3-3D depict a third variant embodiment having the forked wand described above permanently attached at only distal and proximal portion 3d of holder 4, to minimize light dissipation during propagation though wand 4 and holder 4. This structure is most clearly depicted in the cross-sectional views along section lines A-A, B-B and C-C depicted in FIGS. 3B-3D, respectively.

Specifically, along section line A-A wand branches 3a and 3b are permanently attached to holder 4, whereas along section line B-B wand branches 3a and 3b are separate from holder 4, and along section line C-C each of the wand branches 3a and 3b are connected to the proximal portion of holder 4 via a web connection 3k. The reduced thickness of web connection 3k advantageously reduces light dissipation into holder 4.

It should be appreciated that in certain embodiments, wand 3 may have a non-transparent component, or opaque surface layer or film applied to the surface to minimize light dissipation.

FIGS. 4-4B depict an embodiment of the forked wand that is releasable attachable to holder 4, according to a certain embodiment. The connection is accomplished by way of two set of cooperating flex tabs 8, each set disposed on opposite sides of holder 4.

FIG. 4C depicts a cross-section along section lines A-A and depicts wand branches 3a and 3b clamped in between flex tabs 8.

Such a connection configuration also reduces light dissipation through structures connected to wand branches 3a and 3b, thereby preserving available light intensity for illumination ports 7, according to an embodiment.

Figure 5C:
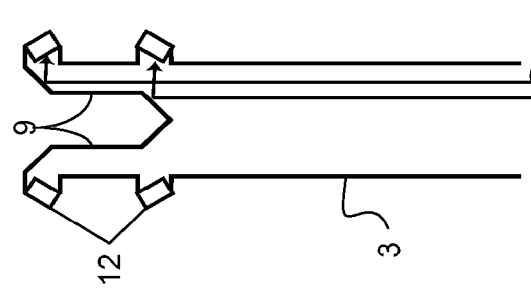
Figure 5B:
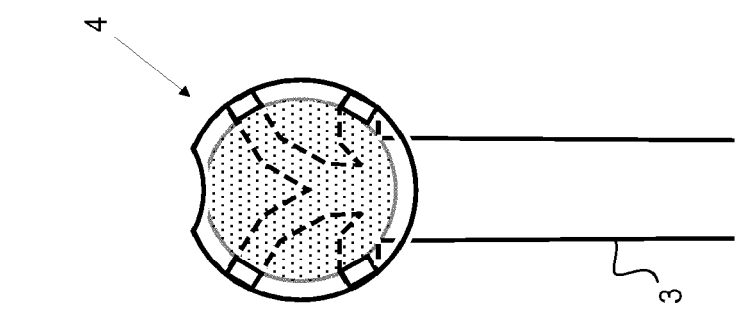
FIG. 5B is schematic, front view of releasably attachable treatment wand in which the holder depicted in FIG. 5 and the wand depicted in FIG. 5A are in a connected state, according to an embodiment.
Figure 5:
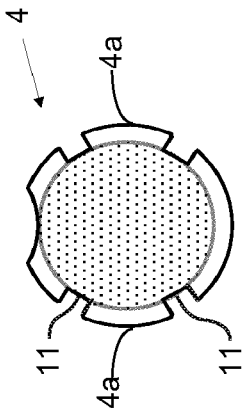
FIG. 5 is schematic, front view of releasably attachable holder having notched connection configuration, according to an embodiment.

FIGS. 5-5D depict additional embodiments of releasably attachable connection configuration for wand 3 and holder 4. Specifically, as shown in FIGS. 5A and 5C wand 3 branches into several wand fingers 9 configured to clip into corresponding notches 11 disposed in holder wall 4a in FIGS. 5B and 5D, respectively.

In certain embodiments wand fingers 9 are implemented with non-circular cross-sections with illumination ports disposed at each distal end 12.

Figure 5A:
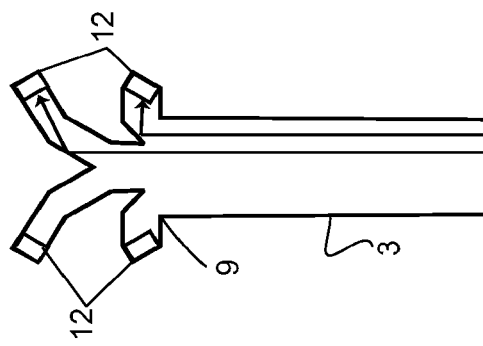
FIG. 5A is schematic, front view of releasably attachable treatment wand having multiple wand branches (fingers) corresponding to the notched connection configuration of the holder depicted in FIG. 5, according to an embodiment.

As shown in FIGS. 5A and 5C, light rays 10 are directed along the length of wand 3 and internally reflected through wand fingers 9 until they exit through illumination ports 12 at the distal end of each of wand finger 9.

It should be appreciated that any feature disclosed in a particular embodiment may be applied to other embodiments.

FIGS. 6 and 6A depict non-limiting embodiments of wand branches having integral light-directing-structures for directing light propagating through the wand branches. Light rays 14 depict schematically a general propagation direction through the light guide.

Specifically, FIG. 6 depicts an embodiment of wand branch 9 having an illumination or emission point 12 at the distal end of branch 9. Reflective surfaces 13 are implemented integrally in branch body 9 so that each reflective surface 13 forms a substantially 45.degree. angle relative to the axis of propagation of the incident light, according to an embodiment. As shown, light propagation is redirected from its incident propagation direction by an angle of about 90.degree. thereby minimizing light dissipation prior to exiting the branch body 9 at distal end 12, according to an embodiment.

FIG. 6A depicts the non-limiting embodiment of wand branch 3a depicted in FIG. 3. Illumination ports 7 are disposed in wand branch 3a directly opposite reflective surfaces 13 so that the propagation direction is redirected through illumination point 7, according to this embodiment.

Embodiments in which reflective surface 13 deviates from the 45.degree. angle relative to the axis of propagation of the incident light, illumination ports are accordingly displaced from a position directly opposite the reflective surface 13 so as to ensure there directed light passes through illumination port 7.

In a certain non-limiting embodiment, each illumination point 7 is implemented as an integrally connected, protruding focusing lens 7 having a substantially convex surface geometry with a radius of curvature focusing light 14 on or near the retina when the device is inserted behind the eyeball.

In certain embodiments, the central of axis 19 of each lens or protruding illumination port is orientated roughly perpendicularly to the sclera so as to minimize the travel path to the retinal to minimize light diffusion through the sclera and the retina and maximize light intensity.

It should be appreciated, however, that embodiments in which the central axis of respective lenses are not disposed at substantially right angles relative to the sclera are also included within the scope of the present invention.

The protruding, convex surface geometry provides certain physiological benefit by advantageously minimizing irritation when the illumination ports 7 contact the sclera during treatment and enhances illumination through coupled light transmittance.

In other non-limiting embodiments, illumination ports 7 are implemented with flat or concave surface geometries having a radius of curvature substantially corresponding to the curvature of the eyeball.

FIG. 6B depicts an variant embodiment of the branch wand of FIG. 6A having an opaque film 3h on selected surfaces of wand body 3m so as to reduce or eliminate light emission from wand body 3m and to allow emission from the illumination ports 7. This configuration advantageously renders illumination ports 7 visually obtrusive to facilitate identification of the radiation-source-material relative to illumination ports 7.

Such opaque films may be applied through dipping the wand into a material like urethane, for example, and then removing the resulting film from designated illumination ports. Alternatively, the desired opaque film may be formed on the wand surface through secondary injection molding as is known to those skilled in the art. It should be noted that the terms "coating" and "film" are used interchangeably in this document.

Figure 7:
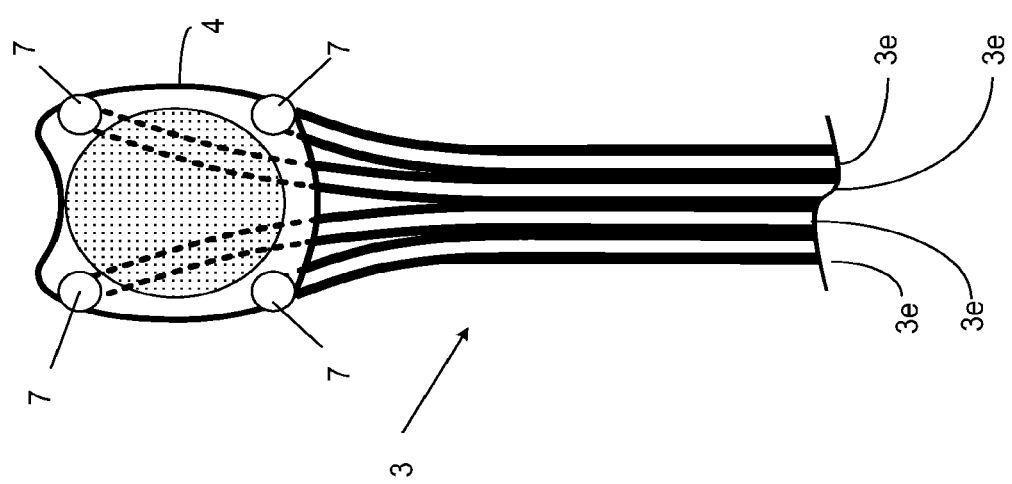
FIG. 7 is a schematic, front view of an alternative embodiment of a wand and holder arrangement in which the wand is implemented as a plurality of stiff hollow tubes configured to receive either fiber optics, or electrical wires when the illumination ports are implemented as light emitting diodes, according to an embodiment.

FIG. 7 depicts an alternative embodiment in which wand 3 is implemented as multiple, hollow branches 3e. In certain embodiments, a concentric fiber optic is disposed in each branch whose distal end is disposed in holder 4 forming the illumination ports 7. In other embodiments, the lumen of each wand branch 3e contains electrical wiring for miniature light emitting diodes (LED) or other light producing electronic devices disposed in holder 4 to generate light beams emanating from illumination ports 7.

It should be appreciated that in some embodiments, a single device may employ any combination of the illumination means like LED's, fiber optics, light pipes, or integral light guide to generate the illumination for the points or ports. Furthermore, it should be understood that in certain embodiments the wand 3 may contain two or more illumination points disposed equidistantly on opposing sides of the holder wall itself or adjacent to the wall in other non-limiting embodiments.

FIGS. 8 and 8A are schematic, transparent perspective and side cross-sectional views, respectively, depicting wand 3 disposed behind eyeball 17 in abutment with optical nerve 17a, to administer a therapeutic dose of radiation into macula 17b from radioactive material 4f contained in holder 4, according to an embodiment.

As noted above, in certain embodiments, wand branches 3a and 3b include illumination ports 7 having convex focusing lenses configured to focus light either on or near the retina. Such lens orientation may be achieved largely through a general concavity of wand branches 3a and 3b that substantially conforms to the contour of eye 17.

The illumination ports 7 may be viewed along lines of vision 19a by way of transpupillary ophthalmoscopy.

As most clearly shown in FIG. 8A, holder 4 is implemented as a disc having a distal surface concavity or notch 20 to receive optic nerve 17a when wand 3 is disposed in a treatment position, according to an embodiment. This configuration provides further guidance to the medical practitioner positioning holder 4 into the proper treatment position by providing tactile feedback upon abutment of holder 4 and optic nerve 17a.

A non-limiting example of such a concavity is one having radius of curvature of about 2.5 mm to 3 mm. Furthermore, concavity 20 advantageously enables radioactive-source material 4f to be placed in maximal proximity to the macula for optimal therapy.

It should be appreciated that notches or slots of a wide variety of geometries suited to the needs and anatomical requirements of the individual patient are also included within the scope of the present invention.

In certain embodiments, holder 4 is implemented without distal notch 20, but rather, with a rounded distal end for application in treatment of intraocular tumors, for example.

In some embodiments, visual support may be further augmented by attaching a sub-miniature video camera and lighting element (such as a fiber optic or an LED) to the distal end of holder 4. This configuration advantageously allows the surgeon to directly view and avoid obstructions in the wand's path during insertion and placement against optic nerves heath 17a.

As noted above, the portion of wand 3 configured for insertion behind eyeball 17 within the orbit of the skull has acceptable ergonomics to minimize patient trauma and surgeon fatigue. Specifically, the insertion portion has a rounded contour, an overall curvature substantially corresponding to the curvature of the eyeball, and is thin; having a maximum thickness of less than about 5.0 mm and width ranging from about 10.0 mm to about 6 mm at the narrowest point in non-limiting examples.

Specifically, FIGS. 9 and 9C depict non-limiting embodiments of holder 4 having a holding cavity 4b facing the eyeball or facing the skull orbit respectively when the wand is disposed in a treatment position.

FIGS. 9A and 9B are cross-sectional views along section line A-A and depict two variant embodiments of the embodiment of FIG. 9.

As shown in FIG. 9A, holding cavity 4b is defined by holder floor 4c and holder wall 4a. Diameter and depth dimensions are defined in accordance with required dimensions of the radioactive source material to be disposed in holder cavity 4b during treatment, according to a certain embodiment. In such lidless embodiments, the radioactive source-material is affixed to holder floor 4c.

FIG. 9B depicts a generally analogous embodiment of FIG. 9A with the addition of holder cover 4e so as to entirely encapsulate a radioactive source material disposed in holder cavity 4b. Sealed holder configurations advantageously enable the radioactive source-material to be implemented as a solid, a powder or even as a liquid, in some embodiments.

Holder cover or lid 4e may be attached to holder walls 4a by glue, ultrasonic welding, or mechanical means like, inter alias, threading or flex tabs.

Holder 4 and holder cover 4e, in some embodiments, are constructed from polymeric materials such as polycarbonate or polysulfone or even metallic materials. Holder cover 4e may have a relatively thickness ranging from 0.1 mm to 1 mm according to certain non-limiting examples.

As noted above, FIG. 9C and the associated cross-sectional views, FIGS. 9C and 9D depict generally analogous embodiments with the exception of the direction of the holder cavity opening. In these embodiments holder walls 4a and floor 4c define a holder cavity 4b opening towards the skull orbit and are otherwise analogous to the embodiments described in FIGS. 9A and 9B.

The holder floor 4c is implemented as a relatively thin polymeric material like polycarbonate or polysulfone having a minimal thickness ranging from 0.2 mm to 1 mm to enable the radiation to effectively penetrate through holder floor 4c into the target tissue, according to non-limiting embodiments.

It should be appreciated that the holder cavity may be implemented in a wide variety of shapes in accordance to the required shape of the radioactive source material.

FIGS. 10A-10B depict a radiation-shielding sleeve 22 slideably mounted on wand 3 to enable a user to slide sleeve along wand 3 into and out of a shielding mode, according to an embodiment. Such functionality advantageously protects a medical practitioners and the patient from radiation during insertion and removal of the radiation device if such protection is deemed necessary.

Specifically, FIGS. 10 and 10A depict shielding sleeve 22 disposed in a shielding, and a non-shielding modes, respectively. When disposed in the shielding mode, sleeve 22 covers radioactive-source-material 4f disposed in holder 4, and, when slid into a non-shielding mode upwards along wand 3, the radioactive source 4a is revealed for treatment.

It should be noted that shielding sleeve 22 is typically constructed of a shielding material like high molecular weight polymer with additives or other materials exhibiting similar functionality, according to non-limiting embodiments.

Typically, the distal area of the shielding sleeve 22 is implemented as thinly as possible to facilitate sliding of sleeve 22 while wand 3 is disposed in a treatment position before and after administration of the therapeutic radiation. It should be appreciated that in certain embodiments, the shielding sleeve remains stationary while the wand and holder 4 slide into and out of treatment position.

Figure 11A:
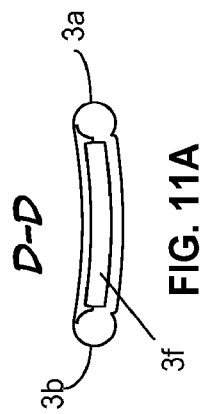
FIG. 11A is a schematic, cross-sectional-view of the lumen along section line D-D, according to an embodiment.
Figure 11B:
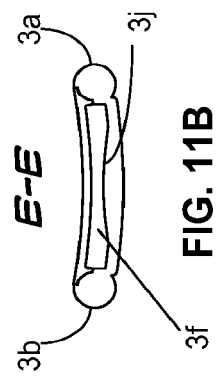
FIG. 11B is a schematic, cross-sectional-view of the lumen along section line E-E depicting a lumen constriction, according to an embodiment.
Figure 11:
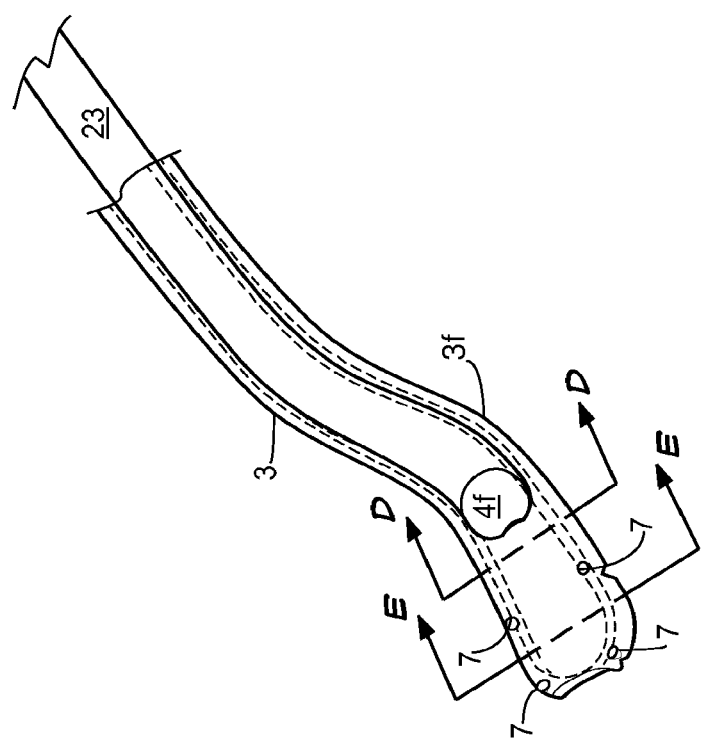
FIG. 11 is a schematic, perspective view of ophthalmic radiation device configured to receive a radiation source into a lumen of a hollow wand, according to an embodiment.

FIG. 11 depicts a wand embodiment configured to facilitate insertion of radioactive source material 4f into the distal end of the wand 3 after it is disposed in a treatment position. As shown, wand 3 is implemented as a relatively flat, hollow tube having lumen 3f (most clearly seen in FIGS. 11A and 11B) through which a solid form of the source material 4f advances when pushed by a semi-flexible inserter 23, according to an embodiment.

FIGS. 11A and 11B are cross-sectional views respectively depicting lumen cross-sectional lumen geometries at section lines D-D and E-E, respectively. As shown in FIG. 11A, lumen has a cross-sectional area sufficient for the passage of source material 4f whereas, at the distal end of wand 3, at section line E-E, the cross-sectional area 3f is constricted by wall bulge 3j. The lumen constriction engages source material 4f in between the lumen walls at the distal end of wand 3, thereby holding it in a treatment position. It should be appreciated that lumen wall bulges or other means of securing source material 4f into a treatment position inside lumen 3f are included within the scope of this invention.

Illumination ports 7 are disposed in a distal portion of the wand and at least partially circumscribe the radiation source material to assist the practitioner in positioning wand 3 into a treatment position as described above.

Figure 12:
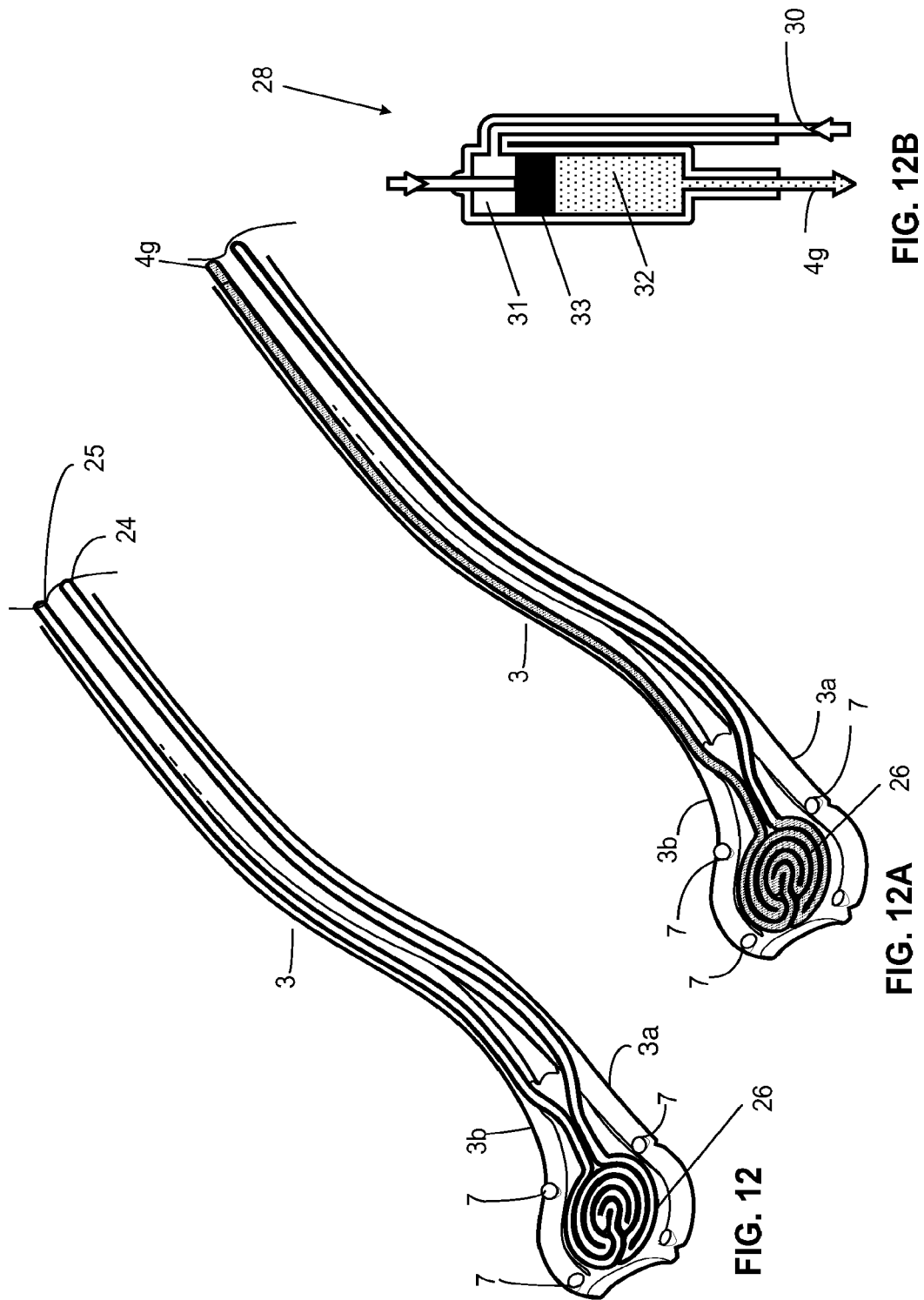
FIG. 12 is a schematic, perspective view of a ophthalmic radiation device having labyrinthine holder configured to receive a liquid therapeutic radioisotope, according to an embodiment.

FIGS. 12-12A depict an alternative embodiment of the wand depicted in FIG. 11 in which liquid radioisotope is injected through passageways leading to either a reservoir or a labyrinthine network disposed in the distal portion of wand 3. It should be appreciated that liquid radioisotopes include, inter alia, suspensions of various types of particulate radioisotopes in a carrier liquid. Examples of carrier liquid include, inter alia, glycerin and water.

Examples of particulate radioisotopes include, inter alia neutron-activated, glass micro-spheres like yttrium aluminosilicate magnesium aluminosilicate, holmium-166, erbium-169, dysprosium-165, rhenium-186, rhenium-188, yttrium-90, or other elements on the periodic table.

In a certain embodiment, the particulate radioisotope is implemented as non-radioactive glass mixed with a radioactive material like, inter alia, iodine-125, palladium-103, and strontium-90 to emit low energy gamma rays.

In another embodiment, the particulate radioisotope is selected from Auger emitters like, inter alia, 67Ga, 99mTc, 111In, 123I, 125I, and 201Tl or from alpha-emitters like, inter alia, uranium, thorium, actinium, and radium, and other transuranic elements.

In yet another embodiment, the particulate radioisotope is implemented as any one or a combination of inter alia $^{89}$Sr, $^{90}$Sr, $^{169}$Yb, $^{32}$P, $^{33}$P, $^{90}$Y, $^{192}$Ir, $^{25}$I, $^{131}$I, $^{103}$Pd, $^{177}$Lu, $^{149}$Pm, $^{140}$La, $^{153}$Sm, $^{186}$Re, $^{166}$Ho, $^{166}$Dy, $^{137}$Cs, $^{57}$Co, $^{369}$Er, $^{165}$Dy, $^{97}$Ru, $^{193m}$Pt, $^{195m}$Pt, $^{105}$Rh, $^{68}$Ni, $^{67}$Cu, $^{64}$Cu, $^{109}$Cd, $^{11}$Ag, $^{198}$Au, $^{199}$Au, $^{201}$Tl, $^{175}$Yb, $^{47}$Sc, $^{159}$Gd, $^{212}$Bi, and $^{77}$As.

As shown in FIG. 12, labyrinthine network 26 is disposed at the distal end of wand 3 in liquid communication with pump 28 of FIG. 12B via passageways 25 and 24. In certain embodiments, the entire liquid delivery system, i.e. pump 28, labyrinthine network 26, and passageways 25 and 24, are implemented as a closed system containing two different liquids; an inert fluid 30 and liquid radioisotope 4g.

As shown in FIG. 12 the inert fluid is initially held in the labyrinthine network 26, and passageways 25 and 24 while the liquid radioisotope 29 is held in a holding chamber 32 associated with pump 28, according to a certain embodiment. When treatment commences, the liquid radioisotope 29 is injected into a passageway 25, designated source material feed line and displaces inert liquid 30 disposed in labyrinthine network 26 which feeds into a secondary holding chamber 31.

Upon completion of the treatment, double piston 33 is driven in the reverse direction to expel the inert liquid 30 from the secondary holding chamber 31 and injects it though passageway 24 into the labyrinthine network 26 where the liquid radioisotope 29 is displaced and returned to holding chamber 33 until the next treatment, according to certain embodiments.

The labyrinthine network 26 advantageously maximizes the quantity of the liquid radioisotope 4g to which the target tissue may be exposed. In certain embodiments pump 28 is disposed at the proximal end of wand 3. A non-limiting example of liquid radioisotope is a Ytterbium suspension and examples of suitable inert liquids include, inter alias, water and glycerin.

FIG. 13-13D all depict light weight handles 2 affording comfortable complete wand control during insertion, removal, and administration of the therapeutic radiation. Regarding illumination sources, FIGS. 13-13C depict various embodiments of illumination or light sources.

Specifically, FIG. 13 depicts a non-limiting handle embodiment in which illumination from an external light source (not shown) is piped into handle 2 through light pipe 6 and coupling 5 disposed at a proximal end of handle 2.

FIG. 13A depicts a non-limiting handle embodiment in which illumination from an external light source (not shown) is coupled in close proximity to the hand grip at an angle non-parallel to the longitudinal axis of handle 2 to advantageously reduce torque FIG. 13B depicts a non-limiting handle embodiment in which illumination is provided from an internal light source disposed inside illumination housing 5a and powered from an external power source (not shown) through electrical cable 6a.

FIG. 13C depicts a non-limiting handle embodiment in which illumination is provided from an internal light and power source disposed inside illumination housing 5a.

It should be appreciated that light control features may also be provided for controlling brightness, color and time responsive audio and video feedback mechanisms configured to alert medical personnel as needed. Such functionality may be provided with the associated hardware known to those skilled in the art, embedded in handle 2 according to certain embodiments or built into the cradle in communication with the handle, according to other embodiments.

It should be further appreciated that in some embodiments respective illumination ports may have light emissions differing in color or frequency from emissions of other illumination ports, and light emission frequencies at each illumination port may be individually variably controlled.

Figure 14:
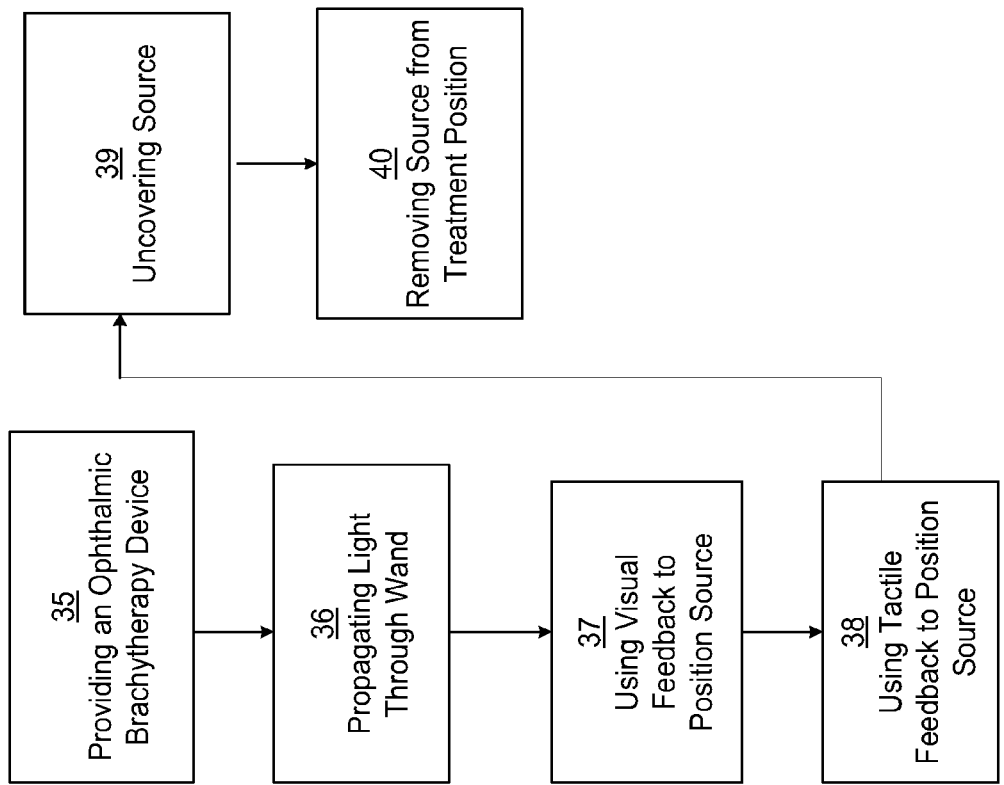
FIG. 14 is a flow chart depicting a process for inserting the ophthalmic radiation device into a treatment position it; according to an embodiment.

FIG. 14 depicts a method for facilitating placement of the radiation source material into a treatment position using visual reference points produced from illumination ports disposed near the radiation source material; according to an embodiment.

Specifically, in step 35, an ophthalmic radiation device having a treatment wand with the above-described light transmitting configuration is provided. In step 36, light is propagated through the wand from an illumination source in the handle to the illuminations ports. In step 37, a medical practitioner placing the device into a treatment position directs the radiation-source holder in accordance with the reference points created from the illumination ports. In step 38, the practitioner employs additional guidance from the tactile feedback resulting from contact of the distal end of the holder with the optical nerve. In step 39, a radiation shielding sleeve is slid towards the handle to uncover and expose the radiation source material in the holder for administration of the therapeutic radiation. In step 40, the device is removed from the treatment position after the source material is covered by the shielding device.

FIGS. 15 and 15A are flow charts depicting treatment steps for devices configured to receive the radioactive-source-material after placement in a treatment position.

Specifically, in step 41 of FIG. 15 in view of FIGS. 11-11B an embodiment of the radiation device having wand lumen is provided. In step 42, wand 3 is positioned into a treatment position. In step 43, the radioactive source material 4f is pushed through the lumen 3f into its treatment position at the distal end of the wand lumen. In step 44, the source material is lodged into place by way of a catch element 3j constricting lumen 3f.

In FIG. 15A, in reference to FIGS. 12-12B, an embodiment of the radiation device including labyrinthine network 26 is provided. In step 46, the wand is inserted into a treatment position. In step 47, a liquid radioisotope is injected into the labyrinthine network 26 through passageways 25 and 24. In step 48 an inert liquid injected into labyrinthine network 26 displaces the liquid radioisotope back into its dedicated storage chamber.

In the next usage, liquid radioisotope 4g is retrieved from the holding chamber and injected into labyrinthine network 26 and inert liquid 30 is displaced into its dedicated storage chamber, according to an embodiment. It should be noted that the injection is accomplished through a driven piston, as noted above.

FIG. 15B is a flow chart depicting a method for facilitating visual identification of a position of a concealed radioactive-source-material based on a visually identifiable reference, according to an embodiment of radiation device.

It should be appreciated that the method may be applied in a wide variety of situations in which radioactive-source-material is concealed and the light beams provide visually identifiable reference.

Specifically, in step 51 a concealed radioactive-source-material disposed in a holder is provided.

In step 52, light is propagated through a substantially light transparent wand.

In step 53, a light beam emanating from the light propagating through the substantially light transparent wand is emitted from each of a series of illumination ports at least partially circumscribing the concealed radioactive-source-material disposed in the holder.

Figure 16:
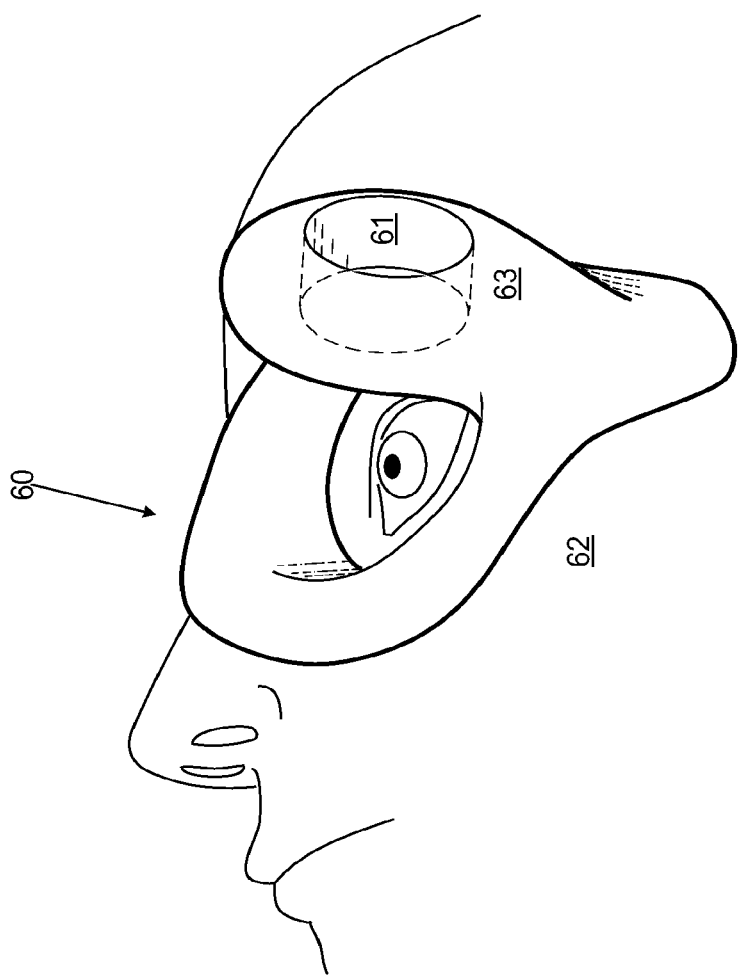
FIG. 16 is a schematic, perspective view of a shielding cradle disposed in a treatment position on a patient's face, according to an embodiment.

FIG. 16 is a schematic, perspective view of a shielding cradle, generally labeled 60, disposed in a treatment position on a patient's face 62 for minimizing radiation exposure to the patients and the medical practitioner, and to provide stability to the device during treatment.

Shielding cradle is constructed of high molecular weight polymers for example, and has a semi-flexible bottom surface configured to substantially form to the contour of the patient's face 62 in certain embodiments. Support element 63 is traversed by a bore 61 configured to receive the handle of the ophthalmic radiation device and to provide a basic direction from which the device will be inserted into a treatment position.

During treatment the cradle is positioned on the patient's face and the wand is inserted through bore 61 and partially supported by support element 63 as the medical practitioner maintains the wand in the treatment position, according to an embodiment.

It should be noted that cradle embodiments lacking radiation shielding capacity are also enclosed within the scope of the present invention.

It should be further appreciated that in some embodiments respective illumination ports may have light emissions differing in color or frequency from emissions of other illumination ports, and light emission frequencies at each illumination port may be individually variably controlled.

It should be appreciated that various combinations of features disclosed in different embodiments are also included within the scope of the present invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

What is claimed is:

1. A device for holding a radioactive source in a treatment position for an eye, comprising:
    a solid wand made of light-transmissive material, the wand configured to direct light from a proximal end of the wand through its length and out of a series of at least four illumination ports at least partially circumscribing a holder, the illumination ports being positioned in a distributed manner radially surrounding the holder;

the illumination ports providing conspicuous points of light during transpupillary viewing, each of the illumination ports includes a convex surface geometry that protrudes outward from a surface of the wand for providing a contact point with a sclera of the eye and configured to channel light substantially near a retina when the substantially light-transmissive wand is disposed in the treatment position for the eye, each illumination port minimizing light diffusion through the sclera while maximizing an intensity of light being emitted by coupled light transmittance that occurs when each illumination port contacts the sclera at a respective contact point with the sclera.

2. The device of claim 1, further comprising a radioactive source disposed in the holder.

3. The device of claim 2, wherein the holder includes an opaque film.

4. The device of claim 1, wherein the light-transmissive wand includes a plurality of engagement configurations operative to provide releasable attachment of the holder.

5. The device of claim 1, wherein the holder is integrally attached to the substantially light-transmissive wand.

6. The device of claim 1, wherein the holder is configured to emit light transmission from a floor of the holder.

7. The device of claim 1, wherein the holder includes a concavity disposed in a distal edge of the holder so as to receive an optic nerve when positioned in a treatment position.

8. The device of claim 1, further comprising a radiation-shielding sleeve slideably mounted to the substantially light-transmissive wand.

9. The device of claim 1, further comprising a handle having a light pipe directing light to the distal end of the light-transmissive wand.

10. A device for delivering a therapeutic dose of radiation to diseased ocular tissue, the device comprising:
a holder; and
a solid light-transmissive wand made of a light transmissive material, the wand configured to direct light from a proximal end of the wand through its length and out of a series of at least four illumination ports disposed around the holder, the illumination ports being positioned in a distributed manner radially surrounding the holder; each of the illumination ports includes a convex surface geometry that protrudes outward from a surface of the wand and configured to channel light, each illumination port minimizing light diffusion through the ocular tissue while maximizing an intensity of light being emitted by coupled light transmittance that occurs when each illumination port contacts the ocular tissue.

11. The device of claim 10, wherein the holder contains a radioactive source.

12. The device of claim 10, wherein the holder includes a concavity disposed in a distal edge of the holder so as to receive an optic nerve sheath when the device is positioned in a treatment position.

13. The device of claim 10, wherein the holder includes one or more connection configurations operative to provide releasable attachment to the wand.

14. The device of claim 10, wherein the holder is integrally attached to the wand.

15. The device of claim 10, further comprising a radiation-shielding sleeve slideably mounted to the wand.

16. The device of claim 10, wherein the holder includes an opaque film coating so as to render only the illumination ports distinct and visually conspicuous during transpupillary viewing.

17. The device of claim 16, wherein the holder includes one or more connection configurations operative to provide releasable attachment to the wand.

18. The device of claim 17, wherein the holder includes a concavity disposed in a distal edge of the holder so as to receive an optic nerve sheath when the device is positioned in a treatment position.

19. The device of claim 18, wherein the holder contains a radioactive source.

20. The device of claim 19, wherein the radioactive source comprises a geometry that matches a geometry of the holder.

* * * * *